Figure 1:
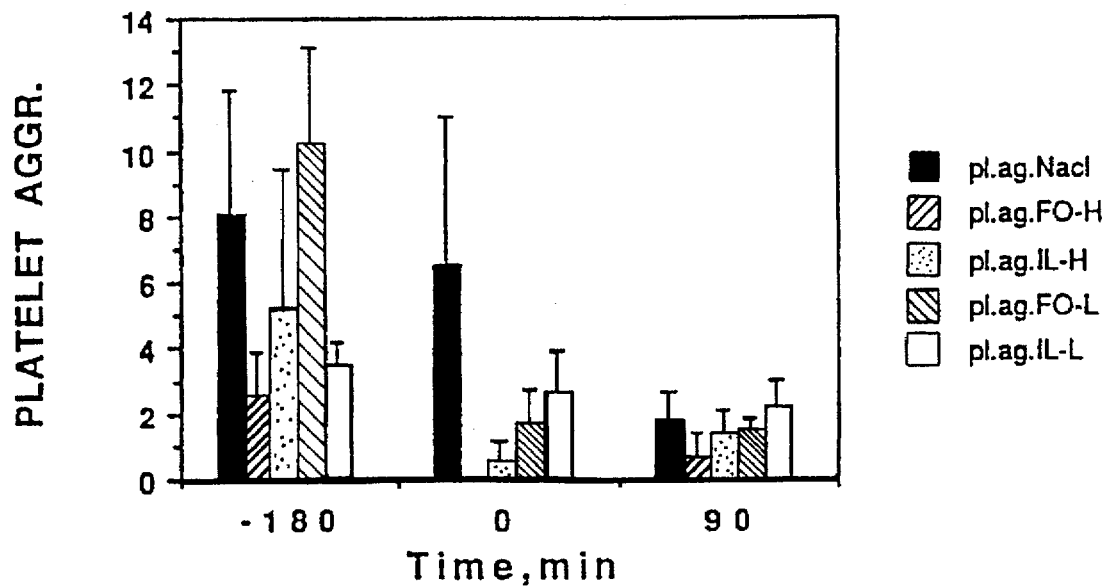

United States Patent [19]

Egberg et al.

[11] Patent Number: 5,731,346
[45] Date of Patent: Mar. 24, 1998

[54] USE OF OMEGA-3-FATTY ACIDS

[75] Inventors: Nils Egberg, Lidingö ; Carin Larsson-Backström, Stockholm; Jan Jakobsson, Djursholm; Rolf Lundh, Huddinge, all of Sweden

[73] Assignee: Pharmacia & Upjohn Aktiebolag, Stockholm, Sweden

[21] Appl. No.: 483,977

[22] Filed: Jun. 7, 1995

Related U.S. Application Data

[62] Division of Ser. No. 290,905, Oct. 21, 1994.

[30] Foreign Application Priority Data

Feb. 24, 1992 [SE] Sweden .................................. 9200541
Feb. 23, 1993 [WO] WIPO ....................... PCT/SE93/00146

[51] Int. Cl.$^6$ ............................................................ A61K 31/22
[52] U.S. Cl. .......................... 514/549; 514/78; 514/458; 514/474; 514/560; 514/824
[58] Field of Search ..................................... 514/549, 560, 514/824, 458, 474, 78

[56] References Cited

U.S. PATENT DOCUMENTS

| | | | |
|---|---|---|---|
| 4,678,808 | 7/1987 | Ward et al. | 514/560 |
| 4,820,731 | 4/1989 | Mascioli et al. | 514/549 |
| 4,960,795 | 10/1990 | Salte et al. | 514/560 |
| 5,223,285 | 6/1993 | DeMichele et al. | 426/72 |

FOREIGN PATENT DOCUMENTS

| | | |
|---|---|---|
| 37 19 097 C1 | of 1988 | Germany . |
| 2 221 843 A | of 1990 | United Kingdom . |
| WO 87/02247 | of 1987 | WIPO . |
| WO 88/01861 | of 1988 | WIPO . |

OTHER PUBLICATIONS

American Journal of Respiratory and Critical Care Medicine, vol. 151, 1995, pp. 1251–1254.

Roberts II et al., Isoprostanes, Novel markers of Endogenous Lipid Peroxidation and Potential Mediators of Oxidant Injury, Annals New York Academy of Sciences, vol. 744, 1994, pp. 237–242.

Endres et al., Measurement of Immunoreactive Interleukin–1β from Human Mononuclear Cells: Optimization of Recovery, Intrasubject Consistency, and Comparison with Interleukin–1α and Tumor Necrosis Factor[1], Clinical Immunology and Immunopathology, vol. 49, 1988, pp. 424–438.

Rubenstein et al., Medicine, New York, 1988, Chapter 5:VI HEMA – Hemostatis and Coagulation, pp. 35–38.

Müller–Berghaus, Pathophysiologic and Biochemical Events in Disseminated Intravascular Coagulation: Dysregulation of Procoagulant and Anticoagulant Pathways, Seminars in Thrombosis and Hemostatis, vol. 15, No. 1, 1989, pp. 58–87.

Putterman, Use of Corticosteroids in the Adult Respiratory Distress Syndrome: A Clinical Review, Critical Care, vol. 5, No. 4, 1990, pp. 241–251.

Esmon et al., Inflammation and Coagulation: Linked Processes Potentially Regulated Through a Common Pathway Mediated by Protein C, Thrombosis and Haemostatis, vol. 66, No. 1, 1991, pp. 160–165.

Dyerberg et al., Eicosapentaenoic Acid and Prevention of Thrombosis and Atherosclerosis? The Lancet – Sat. 15 Jul. 1978, pp. 117–119.

Barcelli et al., Enhancing Effect of Dietary Supplementation With w–3 Fatty Acids on Plasma Fibrinolysis in Normal Subjects, Thrombosis Research, vol. 39, 1985, pp. 307–312.

Hostmark et al., Fish Oil and Plasma Fibronogen, Br. Med. J. (Clin. Res.), vol. 297, 1988, pp. 180–181.

Moncada et al., Nitric Oxide: Physiology, Pathophysiology, and Pharmacology, Pharmacological Reviews, vol. 43, No. 2, 1991, pp. 109–142.

Osterud et al., n–3 Fatty Acids and Pro Coagulant Activities in Circulating Blood, Omega 33 News, vol. V(2), 1990, pp. 1–2.

Egberg et al., Effects of Plasma Kallikrein and Bradykinin Infusions into Pigs on Plasma Fibrinolytic Variables and Urinary Excretion of Thromboxane and Prostacyclin Metabolites, Fibrinolysis, vol. 2, 1988, pp. 101–106.

Bloom et al., Disseminated intravascular coagulation, Haemostasis and Thrombosis, 2nd ed., Churchill Livingstone, London, 1982, pp. 535–540.

Bick, Disseminated Intravascular Coagulation and Related Syndromes: A Clinical Review, Seminars in Thrombosis and Hemostatis, vol. 14, No. 4, 1988, pp. 299–338.

Remedy and Preventive for Thrombosis, JP–A–5978118, vol. 8, No. 184 (C–239) (1979).

Liu et al., Effect of fish oil rich in eicosapentaenoic and decosahexanoic acids on platelet aggregation, coagulation time, and tissue fatty acid compositions in rabbits, Chem. Abs., vol. 111, Abs. No. 22542r 1987.

*Primary Examiner*—Kevin E. Weddington
*Attorney, Agent, or Firm*—Pollock, Vande Sande & Priddy

[57] ABSTRACT

The present invention relates to omega-3-fatty acid containing preparations for the treatment of Disseminated Intravascular Coagulation (DIC) and symptoms related to DIC, as well as such preparations for reducing a pathological increase in pulmonary artery pressure (PAP). The preparations may be in the form of emulsions, or aerosols for inhalation, of an oil or phospholipids or other derivatives or salts of omega-3-fatty acids of marine and/or vegetable origin with a significant content of omega-3-fatty acids. The preparations may also be in tablet or capsule form for oral use.

12 Claims, 3 Drawing Sheets

USE OF OMEGA-3-FATTY ACIDS

This is a divisional application of Ser. No. 08/290,905, filed on Oct. 21, 1994.

The present invention relates to the use of omega-3-fatty acids (hereafter called ω3-fatty acids) for the treatment of or for preventing the development of Disseminated Intravascular Coagulation (hereinafter called DIC; for abbreviations, see the appended Abbreviation List) as well as reducing a pathological increase in pulmonary artery pressure (PAP). The preparations to be used may be in the form of emulsions for parenteral or enteral administration, or for example in the form of aerosols for inhalation or in a form for oral administration. The ω3-fatty acids (or salts or derivatives thereof) can originate from a marine or vegetable oil, from phospholipids, or be of syntheic origin.

BACKGROUND OF THE INVENTION

Today one of the major challenges for intensive care is to combat the secondary hypoperfusion syndromes seen after septicemia, trauma and malignancies. These syndromes include uncontrolled activation of the cascade systems (coagulation, fibrinolyses, kallikrein-kinin-, complement systems) often described as post traumatic micro embolism or disseminated intravascular coagulation (DIC).

Disseminated intravascular coagulation (DIC) gives rise to a wide variety of symptoms, to some extent caused by massive disseminated microembolism. There seem to be various target organs partly due to the inducing agent or cause as well as to probably a number of unknown factors.

A common situation in patients who develope DIC is pulmonary microembolism which could lead to severe problems of gas exchange, oedema and subsequent increase in pulmonary arterial pressure (PAP).

According the literature (Medicine, Edited by E Rubenstein and D D Federman published by Scientific American, New York, 1988, chapter 5:VI, Hemostasis and coagulation, p 35–38) there are a plurality of circumstances that can initiate the DIC-syndrome. Such circumstances may be massive tissue damage, leading to the release of huge amounts of tissue thromboplastic materials, causing extensive activation of the extrinsic system or extensive destruction of endothelial surfaces. The circumstances can be caused by for example severe injuries and infections, tumor products, hemolytic transfusion reactions, vasculitis, heatstroke, hemangomias and certain snake bites. In all cases this leads to a massive activation of the hemostatic mechanisms, which overwhelms the inhibitor mechanisms.

The entire scheme of coagulation either initiated by the intrinsic, including the kallikrein-Factor XII, pathway or extrinsic pathways is finely tuned to culminate in a burst of thrombin activity, causing hemostatic activity at the site of the injury, which leads to deposition of cross-linked fibrin to form a hemostatic plug. Normally, the effects of intravascular coagulation are controlled or modulated by the dilutional effects of the blood flow, by antithrombines, antiplasmin and among other factors the mechanisms that down-regulate hemostasis. However, these control mechanisms can be overwhelmed and disordered by the circumstances mentioned above. This may lead to excessive release of thrombin, which results in thromboses, ischemic conditions and necrosis.

The DIC syndrome can thus lead to massive intravascular deposition of fibrin and impaired nutritive circulation leading to organ failure. This picture of DIC has for a long time dominated the concept of this common disorder. However, alternative views on this syndrome has also been brought forward. The fact that probably several other enzyme systems are involved in the syndrome has been focused on by suggestions on alternate names like "defibrination syndrome". This is discussed in the article of G. M üller-Berghaus in Seminars In Thrombosis and Hemostasis, vol. 15, No. 1, 1989, page 58–87, which is referred to for a review of the numerous conditions related to DIC.

Despite modern treatment modalities, the high mortality rate (>50%) from DIC has not decreased appreciably over the last 20 years. A great number of various therapies have been tried in order to prevent and also treat this syndrome. The treatment of DIC has for a long time been focused on an inhibition of the coagulation process by means of administration of heparin, antithrombin concentrates or hirudin. Depending on the activation mechanism(s) and the dominating symptoms alternative treatments have been suggested like dextran, acetylsalicylic acid, aprotinin, tranexamic acid and even streptokinase. Today corticoid steroid treatment is one of the pharmacological interventions that are frequently tried on these syndromes (C Putterman, J Critical Care 5 (4), 241–251, 1990). Until now however, there has been no consensus how to combat these syndromes. Furthermore there are no scientific proofs for any specific regim in order to prevent this syndrome. Aggressive fracture stabilisation, optimal pain relief and adequate antibiotic therapy is of course of vital importance.

A most interesting report by C Esmon and co-workers (Thrombos Haemostas 66 (1), 160–165, 1991) demonstrated the effect of Protein $C_a$ on an experimental animal model where a disseminated intravascular coagulation was induced by infusion of endotoxin from *E. coli* bacteria. It was shown, that unlike heparin, which only prevented the fibrin formation but not the shock, Protein $C_a$ prevented the development of the whole syndrome. It was further suggested that the dramatic effect of Protein $C_a$ was probably due to a combined inhibitory effect on hemostasis and on the inflammatory reactions included in the endotoxin induced syndrome.

Another approach for the treatment of DIC has essentially aimed at a substitution of consumed coagulation factors and inhibitors. Substitution has been given as full plasma or plasma concentrates of coagulation factors or antithrombin. An adequate treatment of the underlying disease or trauma as well as good general care for circulation and ventilation, has on the other hand been shown to be the most effective way to eradicate this dangerous complication.

Different fatty acids in the lipids have different physiological, biochemical and pharmacological properties and during the last years great interest has been concentrated on the importance of the polyunsaturated ω3-fatty acids, containing 18–22 carbon atoms. The ω3-fatty acids eicosapentaenoic acid (20:5 ω3, EPA) and docosahexaenoic acid (22:6 ω3, DHA) are essential fatty acids in man. Besides their nutritional value, they are also known to possess pharmacological effects. The best known are the cardiovascular effects, the beneficial effects on inflammatory and autoimmune diseases and the necessity of these fatty acids for the normal development of brain and retina functions. These effects have such an importance that a lot of work has been done to find good nutritional compositions containing a high amount of ω3-fatty acids. See e g WO 87/02247 (Baxter) and U.S. Pat. No. 4,820,731 (New England Deaconess Hospital) in which marine oils are used which contain a high amount of the ω3-fatty acids EPA and DHA.

Early observations by Dyerberg et el. (Lancet, ii;117–119, 1978) indicated that there was an association between a high intake of ω3-fatty acids and prolonged bleeding time in Greenland Eskimos. One explanation for the prolonged bleeding time was further shown to be a suppression of the thromboxane $A_2$ ($TxA_2$) synthesis leading to an impaired platelet function. When fish oils are ingested and EPA displaces arachidonic acid (AA), precursor for eicosanoides, from cell membrane phospholipids, eicosanoides from a different series, 3-series, are produced. The thromboxane formed from EPA, unlike that from AA, has very little physiologic activity, whereas the prostacyclin is fully active, leading to an increased total antithrombotic and antiatherogenic prostacyclin activity (Leaf & Weber, n-3 News vol III (4), 1988). However, the ω3-fatty acids in fish oil may influence blood clotting, thromboses and fibrinolysis in many ways.

Tissue plasminogen activator (t-PA) is released from vascular endothelial cells after various kinds of stimuli. Plasminogen is activated by t-PA to plasmin which is the fibrinolytically active enzyme. The thrombolytically active t-PA can cause a dissolution of clots within blood vessels and, thus, prove useful in acute treatment of heart attacs. Dietary supplements for weeks of fish oil has been shown to increase endogenous t-PA production (Barcelli et al, Thromb Res, 39, 307–312, 1985). This action should be the major deterrent to the development of blood clots in coronary arteries which are usually the terminal events blocking blood flow to the heart muscle thus causing heart attacks.

An elevated level of plasma fibrinogen has been identified as a risk factor for coronary artery disease. Dietary intake of fish oil for weeks suppresses the fibrinogen level (Hostmark et el, Br Med I (Clin Res) 297 (6642), 180–181, 1988). Interleukin-1 (IL-1) and tumor necrosis factor (TNF) are both involved in the development of an inflammatory response. Dietary intake of fish oil for weeks has been shown to reduce the production of IL-1 and TNF (Endres et el, Clin Immunol Immunopath, 49, 424–438, 1989).

The endothelial derived relaxing factor (EDRF), recently shown to be identical to nitrogen oxide (NO), has a relaxing effect on vascular smooth muscle and counteracts agents causing vasoconstriction resulting in hypoxic vascular damage. NO has also an antithrombotic and cytotoxic action. The cytotoxicity of activated macrophages against tumor target cells was shown to be dependent on the presence of NO (for references see Moncada et al., Pharmacological Reviews, vol.43, No 2, 1991). Fish oil feeding for weeks is claimed to enhance the effect of EDRF (Vanhoutte et al, In: Health effects of ω3 polyunsaturated fatty acids in seafoods. Eds Simopoulos et al, Karger, 233–244, 1991). Tissue factor (TF), earlier referred to as tissue thromboplastin, is a potent trigger of the extrinsic pathway of blood coagulation. TF is produced by a large number of cell types, though not endothelium. Monocytes can be stimulated by lipopolysaccharides (LPS), which are toxic bacterial material, to expression of TF. Liposomes prepared from soybean lecithin can enhance the LPS effect of inducing thromboplastin in monocytes in the blood. TF expression, as induced by LPS and liposomes, was reduced by 40% after 8 weeks of fish oil diet (Österud et al, Omega-3 News vol V (2),1990). The mechanism for this inhibition probably includes an inhibition of arachidonic acid metabolism to eicosanoides, by cyclooxygenase to prostanoides and by lipoxygenase to leucotrienes (Österud et al, Abb Med, 21, 47, 1989). Non-steroidal anti-inflammatory drugs (NSAID), like acetylsalicylic acid, however, block only the cyclo-oxygenase and thereby provide more substrate for the lipoxygenase pathway, leading to 50–250% enhanced monocyte activation as expressed by induced thromboplastin activity. Thus, to create an inhibition on inflammatory reactions as well as on blood coagulation, fish oil might be a better treatment than NSAID.

The above mentioned mechanisms are involved in reactions which may lead to the DIC syndrome.

In an animal experimental model we have previously studied a DIC-like syndrome induced by infusion of plasma kallikrein (Egberg et al, Fibrinolysis, 2, 95–100; 101–106, 1988). In the initial studies we followed the plasma concentrations of prekallikrein and free kallikrein activity as well as coagulation factor XII and fibrinogen. The major inhibitor of plasma kallikrein, $C_1$-esterase inhibitor, as well as antithrombin, $\alpha_1$-antitrypsin and $\alpha_2$-macroglobulin were also determined. Fibrinolytic variables like plasminogen and $\alpha_2$-antiplasmin were additionally followed. The conclusions drawn from these studies were that a slowly professing DIC was induced leading to a small but progressive consumption of coagulation factors. There was also a progressive consumption of $\alpha_2$-antiplasmin, indicating a comparatively intense activation of the fibrinolytic system. These findings lead to the conclusions that we should look closer for a possible platelet activation. This was done by following the urinary excretion of the major thromboxane $A_2$ metabolite, 2,3-dinor-tromboxane $B_2$. Thromboxane $A_2$ is synthetized by platelets after various types of platelet stimulation and is one of the most powerful platelet aggregating agents known. At the same time we followed the urinary excretion of the major metabolite of prostacyclin, 2,3-dinor-prostaglandin $F_1$a. Prostacyclin is synthetized and released from the vascular endothelium and is possibly the most effective inhibitor of platelet aggregation in the body. We also decided to look at the activation of the fibrinolytic system by measuring the plasma level of tissue plasminogen activator, t-PA.

In the previous study on a DIC-like syndrome we found a rise of the urinary excretion of thromboxane and prostacyclin metabolites after the kallikrein injections, indicating that the arachidonic acid metabolism was stimulated. The increased excretion rate for thromboxane metabolites suggested an in vivo aggregation of platelets that could contribute to the syndrome developed. A marked fall of the leucocyte count, which may be explained by aggregation of leucocytes, was also found. We also found an increase of the plasma level of t-PA, which probably was the cause of the earlier observed signs of activation of the fibrinolytic system. Of the cardiovascular parameters measured pulmonary artery pressure (PAP) increased and blood pressure (BP) was reduced.

DESCRIPTION OF THE INVENTION

We have found surprisingly that preparations containing ω3-fatty acids have extraordinarly advantageous effects for the treatment of DIC including a reduced pathological increase in pulmonary artery pressure (PAP).

In the present investigation we have studied the changes in the hemostatic system in a DIC model induced by injection of plasma kallikrein after pretreating the animals with marine oil emulsion.

We claim the use of ω3-fatty acids for the preparation of a medicament to be useful in the treatment of, or for preventing the development of DIC or for reducing the pathologically increased PAP. The ω3-fatty acids may come from marine oils, vegetable oils rich in ω3-fatty acids or from phospholipids containing ω3-fatty acids. The ω3-fatty-acids may also be in the form of synthetic derivatives or salts thereof.

Suitable administration forms are emulsions for parenteral, peroral or oral use, where the emulsions may be of therapeutic value or adapted for TPN (Total Parenteral Nutrition). Other suitable administration forms are inhalable aerosols, dosage forms to be administered nasally and orally in the form of tablets and capsules. The preferred ω3-fatty acids are EPA and/or DHA or their salts or derivatives.

The beneficial effects of fish oil after oral administration are first obtained after weeks of treatment. In order to reduce the incidence of DIC, which is mostly an acute situation, the effects of fish oil should be obtained with a short onset of action. The ω3-fatty acids ought therefore to be active in some intravenously or inhalalable active and tolerable administrative form.

In the present invention we have used ω3-fatty acids in a preparation derived from marine oils in the form of an oil in water emulsion as prepared and presented below in Example 1. It must be clearly stated that other preparations containing ω3-fatty acids or derivatives thereof must be considered to be useful in the treatment of DIC. Such preparations may be types of emulsions or solutions other than specified in Example 1, with more concentrated ω3-fatty acids, with appropriate diluents or carriers, as well as oral preparations containing the ω3-fatty acids as salts of glycerol- and ethyl esters, phospholipids or sterols or other derivatives of ω3-fatty acids and suitable exdpients. The oral preparations may be in conventional tablet form or in capsules manufactured according to well known techniques.

As alternatives to the mentioned preparations aerosols can be effective, both in a conventional form and in a form where the ω3-fatty acids are comprised in eventually bilayer forming phospholipids (liposomes) and different nasal preparations. The aerosols are intended to be adminstered by inhalation to the lungs, but may also be adapted to be administered through the nasal mucous membranes.

Useful emulsions could comprise 0.5–50% (w/v of total emulsion) oil, preferably 5–30% (w/v), vegetable oils, such as soybean oil, coconut oil, cottonseed oil, safflower oil, sunflower seed oil, linseed oil, borage oil, blackcurrent seed oil, canola oil or other vegetable oils containing ω3-fatty acids, or marine oil, or a mixture of those mentioned. The amount of the phospholipids could be 0.1–80% (w/v of total emulsion), preferably 0.1–20% (w/v). The preparation should contain ω3-fatty acids or derivatives thereof to an amount of 0.5–100%.

Phospholipids such as egg yolk or soybean phospholipids, marine phospholipids or synthetic emulsifiers can also be included in the emulsion. The total amount of emulsifier is preferably 0.1–20% (w/v of total emulsion). The emulsion can also contain other components which are normally incorporated in emulsions e.g. monoglycerides of fatty acids, components for adjusting isotonic properties (such as glycerol), antioxidants such as α-tocopherol, components for adjusting stability such as amino acids, and carbohydrates such as fructose and glucose etc.

Antioxidants should be added to protect the unsaturaed ω3-fatty acids from oxidation. Such antioxidants could be α-tocopherol (Vitamin E), Vitamin C, carotenoides or retinoides. However, other antioxidants can be used which are active to protect the unsaturated ω3-fatty acids from oxidation in the preparation, after administration and after incorporation into biological membranes. A study of antioxidants in marine oil emulsions has been performed and is presented in Example 2 below.

The preparation of the emulsion is carried out in a conventional manner. Thus the lipids are mixed with the aqueous phase, phospholipids and optionally other emulsifiers and auxiliary agents in a suitable mixing device. Then the blend is homogenized to a desired particle size, preferably less than 1 micron. The ways to adjust the emulsion to a suitable particle size is well known to a person skilled in the art.

DIC is frequently still seen in combination with major trauma, septicemia, meningoencephalitis and pancreatitis. There is often, however, a 12–26 hours elapse between the onset of symptoms and the debut of coagulation and respiratory distress. Major efforts are today spent on therapeutic manoeuvres in order to prevent these disorders from appearing, by early fracture stabilisation, antibiotics, pain management, stress reduction and the goal is also to optimize oxygen delivery. Still these syndromes appear in a non-systematic fashion and with a high frequency of most complicated course. Therefore it seems most interesting, that some therapy could be given in advance to most patients at risk, with the potential effect of lowering the incidence of DIC.

We have now found that preparations containing ω3-fatty acids have advantageous effects for the prevention of or the treatment of DIC, so that the incidence of DIC will be reduced. The DIC syndrome may be a syndrome as such or included in other syndromes like pulmonary microembolization, multiple organ failure (MOF), sepsis and other infectious and ischemic conditions. The effects of ω3-fatty acids are seen very early, already after two hours of infusion, and can thus be of value for treatment and prevention of the development of the DIC syndrome and to reduce the incidence of DIC and related syndromes, which mostly are acute situations.

The preparations containing ω3-fatty acids will also be useful in the treament of DIC-related symptoms and condtions, such as incresed pulmory arterial pressure (PAP) and those described in the articles in Seminars In Thrombosis And Hemostasis vol. 14, No. 4, 1988, pages 299–338 (R L Bick) and in Seminars In Thrombosis And Hemostasis vol. 15, No. 1, 1989, pages 58–87 (G Müller-Berghaus).

The ω3-fatty acids in fish oil may influence on blood dotting, thrombosis and fibrinolysis in many ways. The beneficial effects of fish oil is relevant for the treatment of the DIC syndrome. The ω3-fatty acids may reduce the hemostatic changes so that coagulation, fibrinolysis and thrombosis parameters are kept in balance. The end points of these effects are reduction of fibrin deposits, reduced microembolism and reduced tendency for increased pulmonary artery pressure and to prevent a decrease in $PaO_2$. In subchronic/chronic cases of DIC (see Seminars In Thrombosis And Hemostasis, vol. 14, No. 4, 1988, R. L. Bick), of which some patients are treated with total parenteral nutrition (TPN), e.g. malignancies (gastrointestinal, pancreas, prostate, lung, breast), chronic inflammatory disorders (Chrons disease), the effects of ω3-fatty acids may be obtained in lower doses administered for a longer period of time. In more acute situations with DIC (see the mentioned article of R. L. Bick, 1988), e.g. bacteremia, burns, disseminated malignancy, liver disease, vascular disorders, the effects of fish oil should be elaborated rapidly enough to be of value to reduce the incidence of DIC.

In order to obtain an acute effect the ω3-fatty acids should be administered intravenously in the form of an emulsion. The acute effect should appear within hours and therefore the dose needed can be expected to be relatively high. In the experiments performed and presented below in Example 4 it is shown an improvement of the DIC syndrome already after a two hour infusion of marine oil emulsion. The PAP and thus the ventilatory complications associated with DIC in the lungs were reduced, $PaO_2$ was maintained, the tendency of the platelets to aggregate was minimized, the fibrinolytic response was increased and no fibrin deposits could be found in any of the organs tested (kidney, lung, heart and spleen). The reduced level of fibrinogen, seen after only two hours of infusion of marine oil emulsion, may together with other positive effects shown for ω3-fatty acids, minimize the vulnerability for heart attacks. The reduction in RBC viscosity indicates increased nutritional blood flow through the capillaries. The positive effects on hemostasis are obtained before, and with a lower dose than that needed to suppress the immune defence.

The positive effects on hemostasis and DIC are obtained after a short single infusion, which together with the anti-inflammatory effects expected after repeated infusions may have wide implications on DIC related symptoms. This anti-inflammatory effect is in favour over that obtained with NSAID:s, since these drugs block only cyclo-oxygenase and thereby provides more substrate for the lipoxygenase pathway, leading to enhanced monocyte activation as expressed by increased lipoxygenase effects and induced tissue factor activity. A concomitant vasodilation and increase in nutritional blood flow, reduction in PAP and maintained $PaO_2$ is a great and totally unexpected advantage compared to present treatment with vasodilators, which usually reduce $PaO_2$. This, together with increased fibrinolysis, reduced thrombogenicity and fibrin deposits, and the rapid onset of action enables the long-chain polyunsaturated fatty acids a unique and unexpected possibility to treat and prevent the development of DIC.

Lipid emulsions or other preparations containing ω3-fatty acids, such as aerosols for inhalation, containing ω3-fatty acids, are useful therapeutically to treat severe trauma and to treate and help to prevent the development of various forms of DIC. Such emulsions are also nutritionally useful, for example to patients with DIC, who also need parenteral nutrition (TPN) for a shorter period, or in long term TPN to reduce the symptoms of more chronic forms of DIC.

The invention thus relates to the use of ω3-fatty acids or their derivatives in emulsions or in other preparations with therapeutic effects for various forms of DIC and DIC-related symptoms as incresed PAP or to reduce the incidence of these symptoms and also, in combination with TPN, to these patients. The administration form can be by parenteral infusion or inhalation of aerosols containing ω3-fatty acid rich phospholipids or nasal preparations to thereby obtaining acute as well as chronic, long-lasting effects, or by peroral or oral administration in more chronic situations with DIC or in inhalations of liposomes as ω3-fatty acid containing phospholipids to reduce the risk of complications related to pulmonary microembolization. The doses of ω3-fatty acids to be administered in an acute situation (1–2 days) may be high in order to approach. The level of the therapeutic window. For therapeutic use over a longer time period with repeated administration the dose of ω3-fatty acids may be reduced to approach the amount of ω3-fatty acids which should be of not only therapeutic but also of nutritional value. For nutritional use in TIN the ω3-fatty acids should be administered together with other fatty acids.

Various modifications and equivalents of the emulsion or other forms of therapeutic preparations will be apparent to one skilled in the art without departing from the spirit or scope of the invention. It is therefore to be understood that the invention is not to be limited to the specific examples and embodiments disclosed herein.

EXAMPLES

Example 1

Preparation of an emulsion containing fish oil and egg yolk phospholipids

The emulsion contained:

| | |
|---|---|
| Fish oil | 200 g |
| Egg yolk phospholipids | 12.0 g |
| Glycerol | 22.2 g |
| Aq. ad inject. | 750 g |
| NaOH, 1 M | 1.3 ml |

As antioxidant vitamin E (α-tocopherol) was added to the emulsion in an amount stated in me respective example.

The ingredients above were mixed in a "Ultra Turrax" and thereafter homogenized in a "Moulin-Gaulin High Pressure Homogenizer" The fish oil used had the following fatty acid content in %:

| 14:0 | Myristic acid | 6.3 |
|---|---|---|
| 16:0 | Palmitic acid | 14.7 |
| 16:1 (ω7) | Palmitoleic acid | 7.3 |
| 18:0 | Stearic acid | 2.6 |
| 18:1 (ω9) | Oleic acid | 8.9 |
| 18:1 (ω7) | Vaccenic acid | 3.1 |
| 18:2 (ω6) | Linoleic acid | 1.1 |
| 18:3 (ω3) | Linolenic acid | 0.7 |
| 18:4 (ω3) | Stearidonic acid | 2.6 |
| 20:1 (ω9) | Eicosenoic acid | 1.5 |
| 20:4 (ω6) | Arachidonic acid | 1.4 |
| 20:5 (ω3) | EPA | 17.8 |
| 22:1 (ω11) | Docosaenoic acid | 2.2 |
| 22:5 (ω3) | Docosapentaenoic acid | 2.9 |
| 22:6 (ω3) | DHA | 13.5 |

Total amount of fatty acids: 100% (w/w).

The egg yolk phospholipids used had the following fatty acid content in % of total fatty acids (w/w):

| 14:0 | Myristic acid | 0.2 |
|---|---|---|
| 16:0 | Palmitic acid | 31.5 |
| 16:1 (ω7) | Palmitoleic acid | 1.2 |
| 18:0 | Stearic acid | 14.1 |
| 18:1 (ω9) | Oleic acid | 28.0 |
| 18:2 (ω6) | Linoleic acid | 12.4 |
| 20:1 (ω9) | Eicosenoic acid | 0.2 |
| 20:4 (ω6) | Arachidonic acid | 4.2 |
| 22:6 (ω3) | DHA | 5.8 |

Example 2

Evaluation of MO-em in a DIC model and comparison with Intralipid®

As a conclusion of previous experiments the most relevant way to follow the changes reflecting the DIC syndrome as induced by plasma kallikrein appear to be to perform consecutive determinations of the following hematological and hemostatical parameters: Fibrin monomer (FM, soluble fibrin); white blood cell count; fibrinogen; t-PA and α2-antiplasmin. Since platelets are most likely to be affected by the kallikrein (KK) injections, as indicated by the thromboxane metabolite excretion, it would probably be of interest to study to what extent this also affects the platelet function. Consecutive determinations of platelet aggregation ought to be included in a new study. In addition the cardiovascular parameters PAP, indicating the respiratory involvement of the DIC syndrome, BP, cardiac output (CO), heart rate, left ventricular pressure (LVP) and blood gases should be followed to reflect the involvment of the cardiovascular system.

Experimental Procedure

Pigs, mean weight 26.3 kg, range 22–32 kg, n=19 were used for the experiments. The animals were given ketamin, 500 mg, (Ketalar, Parke-Davis, Morris Plains N.J.) intramuscularly as a premedication. Anesthesia was induced with penthobarbital sodium, 5 mg/kg bw (Mebumal vet, ACO Stockholm Sweden) given intravenously and maintained with a continous infusion of fentanyl, 10 mg/kg bw/h (Leptanal, Jansen Leo Pharma AB, Helsingborg, Sweden) and pancuroniumbromide, 0.2 mg/kg bw/h (Pavulon, Organon, Oss, Netherlands). After induction of anesthesia the animals were all intubated and mechanically ventilated with an Engstrom respirator to an arterial carbon dioxide partial pressure of approximately 5 kPa with a gas mixture of $O_2$ and $N_2O$ 1:2. Catheters were placed in the mid aorta and inferior vena cava through a femoral cut down. A 7F triple-lumen catheter (Swan-Ganz, American Edwards Laboratories, Irve St Ana, Calif.) was introduced through a cut down to the right external jugular vein. Through a midline abdominal incision catheters were introduced into both ureters for control of diuresis and collection of urine. Arterial mean pressure (MAP), pulmonary artery mean pressure (PAP) and pulmonary capillary wedge pressure (PCWP) were recorded with capacitive transducers which were positioned at mid-thoracic level. All recordings were made with a Polygraph (Model 7B, Grass Instruments, Quincy, Mass.). Arterial blood was drawn for blood gas analysis, made directly after sapling with a standard electrode technique (ABL 2, Radiometer, Copenhagen, Denmark) The animals were hydrated with isotonic saline to a stable wedge pressure. Cardiac output was measured by thermo dilution technique and a cardiac output computer was used for the calculations (model 9310 Edwards laboratories).

After the first blood sample was drawn and during the animal preparation a pretreatment period with infusions was started. During this period the animals received a high dose, 10 ml/kg bw, or a low dose, 5 mL/kg bw of lipid emulsion (see Example 1). The control group recieved 10 ml/kg bw of physiological saline solution and in order to give equivalent volumes to all animals the total dose of lipid emulsion and saline was adjusted to 10 ml/kg bw. These infusions were given over a 2-hour period after which there was a 1-hour stabilizing period before the kallikrein injection. Blood and urine were sampled before and 1 hour after infusions of lipid emulsions or saline (before kallikrein injection), and 30, 90 and 180 minutes after kallikrein injection.

Swine plasma kallikrein was isolated from pig plasma according to Gallimore et al (Thromb Res, 2, 409–420, 1978). It was dissolved in buffered saline to the concentration 0.9–1.1 units/ml (one unit is defined as the activity generated by total activation of the prekallikrein in 1 ml of pooled normal human plasma). Plasma kallikrein was diluted in 60 ml physiological saline and given as three 20 ml i v infusions over one minute at five minute intervals, in a total dose of 0.33 units/kg bw.

Experimental groups and dosing

| NaCl: | Physiological saline, (control) 10 ml/kg bw, 0.08 ml/kg bw/min | | |
|---|---|---|---|
| FO-H: | Marine oil emulsion, high dose | -"- | -"- |
| IL-H: | Intralipid® 20%, high dose | -"- | -"- |
| FO-L: | Marine oil emulsion, low dose, 5 ml/kg bw, 0.04 ml/kg bw/min | | |
| IL-L: | Intralipid® 20%, low dose | -"- | -"- |

There were four animals in each group, except in the control group, there were three. The emulsions were prepared as described in Example 1.

The preparation of the emulsions was carried out in a conventional manner. The composition and preparation of marine oil emulsion is described in Example 1. Intralipid® contains 20% (w/v) oil as soybean oil and 1.2% (w/v) egg yolk phospholipids.

The infusion rate was four times higher than that recommended in normal clinical practice.

Methods

White blood call count as well as hematocrit determinations were performed in an electronic cell counter (Contrave Autolyzer 801, Zürich, Switzerland)

Fibrinogen was determined with a polymerization rate assay (Vermylen et al, Clin Chir Acta, 8, 418–24, 1973).

Soluble fibrin (fibrinmonomer) was determined by means of an amidolytic assay according to Wiman and Rånby (Thromb Haemostas, 55, 189–193, 1986) utilizing kits from KabiPharmacia.(Stockholm, Sweden, Coa-Set FibinMonomer)

Tissue plasminogen activator (t-PA) was determined by functional spectrophotometric methods utilizing kits from Biopool AB (Umeå Sweden, Chmielewska et al, Clin Chem, 32, 482–485, 1986).

Alpha$_2$-Antiplasmin was determined by an amidolytic assay (Contest Antiplasmin, KabiPharmacia, Stockholm, Teger-Nilsson et al, J Clin Lab Invest. 47, 403, 1977).

Whole blood platelet aggregation was performed with ADP, 5 µmol/l final concentration, in a Chrono-Log Whole Blood Agregometer (Coulter Electronics Ltd, Luton, UK, Cardinal et al, J Pharmacol Methods, 3, 135–137, 1980).

2,3-Dinor-thromboxane $B_2$ and 2,3-dinor-prostaglandin $F_1$ a, the major urinary metabolites of $TxA_2$ and prostacyclin, were determined with quantitative gas chromatography and mass spectrometry Vesterqvist and Gréen, Thromb Res, 33, 39–49, 1983; Prostaglandins 28, 139–154, 1984).

Blood samples. Arterial blood was drawn from an indwelling catheter. Nine parts of blood was mixed with one part trisodium citrate solution, 0.129 mol/l. Plasma was harvested after centrifugation and stored frozen at −70° C. until analysis. Immediately after drawing and mixing with citrate solution, 1 ml of blood was taken for t-PA analysis and mixed with 0.5 ml sodium acetate buffer, 1 mol/l, pH 3.9. After centrifugation the supernatant was taken and stored at −70° C.

Urine samples were obtained through catheters inserted into the ureters. A zero value was obtained by collecting the urine standing in the bladder.

Histopathology. Material fixed in 4% buffered neutral formaldehyde was received from the following organs: kidney, lung, heart and spleen (only one pig). The material was embedded in paraffin, sectioned in 4–5 µm sections and stained with haematoxylin-eosin (HE), phosphotungstic acid haematoxylin (PTAH) and Martius scarlet blue (MSB). The two latter stains were used to demonstrate fibrin (Mallory, Pathological Technique, Saunders, 1938; Lendrum et al, J Clin, Path, 15, 401–413, 1962). The sections were examined under the light microscope. The treatments of the pigs were unknown to the examiner at the time of microscopical examination.

Results

Haematology

Effects on white blood cell count

The white blood cell count generally increased during the combined surgery, stabilizing and lipid infusion period as a response to the surgical trauma. After infusion of kallikrein the animals receiving control infusion or MO-em showed a progressive reduction of the white cell count reaching pre-infusion level at 90 minutes post-(KK) infusion. At 180 min post-KK-infusion WBC count increased again in the placebo group, whereas it remained essentially stable in the other groups.

Platelet function tests Platelet aggregation was reduced in all groups receiving lipid infusion except the low dose Intralipid® group, while it was essentially unchanged in the control group during the pre-kallikrein period, see FIG. 1. In the high dose MO-em group platelet aggregation was completely abolished after the lipid infusion. At 90 minutes after the kallikrein injection, the platelet aggregation was lower in the control group than during the prekallikrein period but essentially unchanged for the lipid treated groups. The high dose MO-em and Intralipid® groups had regained some aggregately at 90 minutes post-kallikrein. The decrease in platelet aggregability at 90 minutes post-kallikrein may be explained by refractoryness and/or inhibition. In the control group, having high aggregability left before the kallikrein injection, many of the platelets may be refractorial to a new aggregation. However, in the MO-em groups, and possibly me high dose Intralipid® group the aggregability was low before the kallikrein injection, indicating inhibition which remained also at 90 minutes post-kallikrein. The results show that even a short-lasting infusion of MO-em reduces platelet aggregation.

The main urinary metabolites of thromboxane (MIM-TXA) and prostacyclin (MUM-PGI) were slightly increased by kallikrein injection. This increase was not reduced by a short-lasting infusion of MO-em, at least not as measured in urine. The possibility remaines, however, for a local reduction.

Blood coagulation

The fibrinmonomer (FM), soluble fibrin, is a good marker for a generalized blood coagulation in vivo. FM was increased in all groups 30 minutes after kallikrein injection, indicating increased disseminated coagulation. The inability to show reduced blood coagulation 30 minutes after kallikrein injection and only 90 minutes after completed infusion of lipid emulsions may be explained by the remaining phospholipid vesicles in the blood (Österud et al, 1990). The reduction in coagulability is however seen after oral (Österud et al, 1990) administration of marine oil or 1 to 2 days after intravenously infused marine oil emulsion.

Fibrinolytic variables

Figure 2:
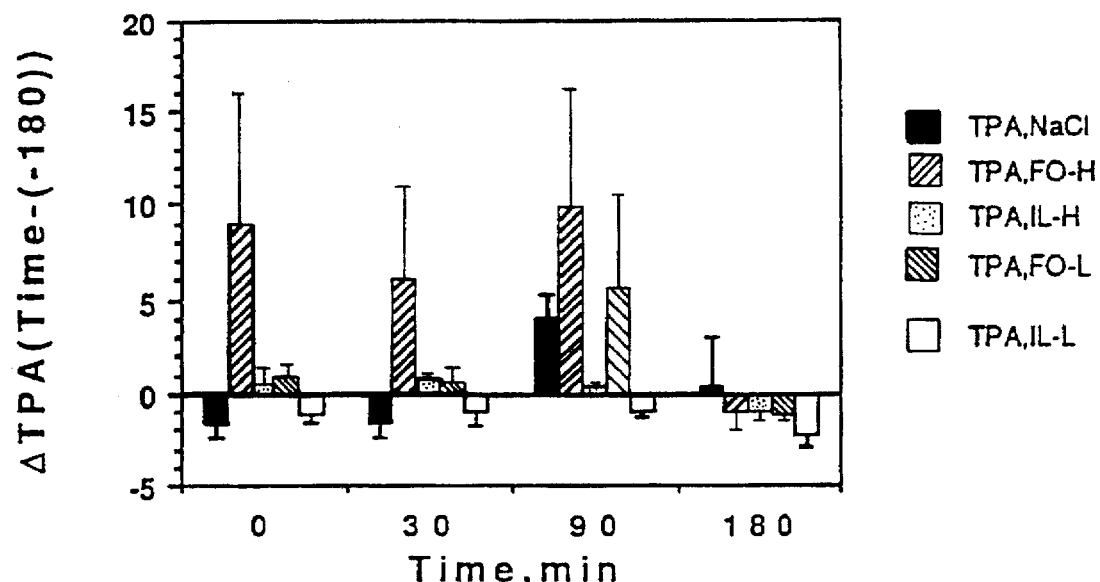

Tissue plasminogen activator (t-PA) is released from vascular endothelial cells after various types of stimuli. t-PA activates plasminogen to plasmin with fibrinolytic activity. An increase in t-PA was seen after kallikrein injection, with a maximum at 90 min. This increase was seen after infusion of MO-em in both doses but not after Intralipid®. During the pre-Kallikrein period after infusion of MO-em in high dose t-PA was increased to a level higher than the other groups, indicating stimulation of t-PA release, resulting in incresed fibrinolysis. This was not seen after infusion of Intralipid®. At 180 minutes post-kallikrein the levels were normalised in all groups, see FIG. 2.

Figure 3:
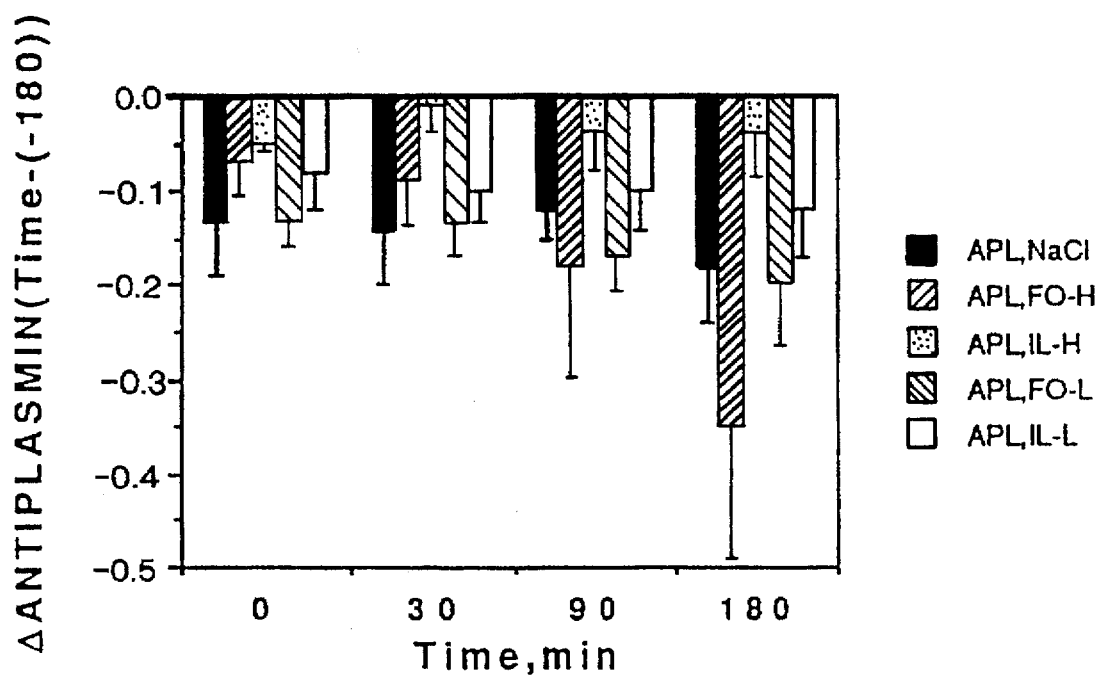

Antiplasmin which inactivates plasmin, was reduced 180 minutes after kallikrein injection, see FIG. 3. This reduction was similar in the MO-emulsion and the placebo groups. However, in the group which received a high dose MO-emulsion, antiplasmin was reduced more markedly, reflecting an increased plasmin generation and a more prominent fibrinolytic response. During the pre-kallikrein period, antiplasmin was reduced in all groups, indicating increased fibrinolysis, probably mainly due to surgery.

Figure 4:
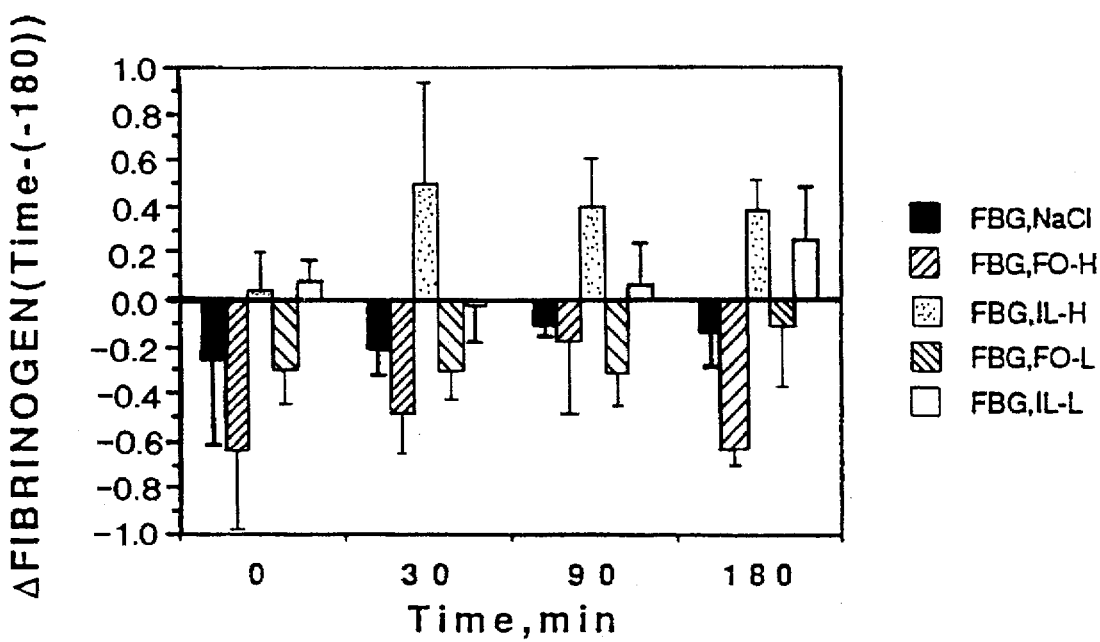

Fibrinogen which is converted to fibrin by the action of thrombin, was reduced in the control and MO-em groups during the pre-kallikrein period, presumably caused by the surgical trauma, see FIG. 4. The level remained low also after kallikrein injection. At 180 minutes post-kallikrein the level of fibrinogen was lower in the FO-H group than in the other group.

Histopathology

The number of pigs examined in each group was: two controls, four high dose MO-em, four high dose Intralipid®, three low dose MO-em and three low dose Intralipid®.

There was presence of fibrin-like material in small blood vessels in the heart in one of the two control pigs and in one of four pigs given the high dose and one of three pigs given the low dose, respectively, of Intralipid®. The deposition of fibrin-like material was slight in all three cases. Deposition of fibrin-like material was not observed in any pig given the MO-em.

To observe microthrombi formation in the circulation by light microscopy after only three hours of induction of DIC may be difficult and probably explain the relatively slight morphological manifestation of DIC in this study. MSB and PTAH stains are recommended in the diagnosis of DIC (Hamilton et al, J Clin Path, 31, 609–619, 1978; Skörten, Acta Path Microbiol Scand, 61, 405–414, 1964) although immunological methods are more specific. A few spontaneous changes were recorded in some pigs but were considered to be without importance for the evaluation of the effect of treatment of lipid emulsion in DIC.

In conclusion, no evident light microscopically visible morphological manifestations of fibrin depositions in the tissues examined from the MO-em treated pigs could be observed.

Cardiovascular Parameters

Figure 5:
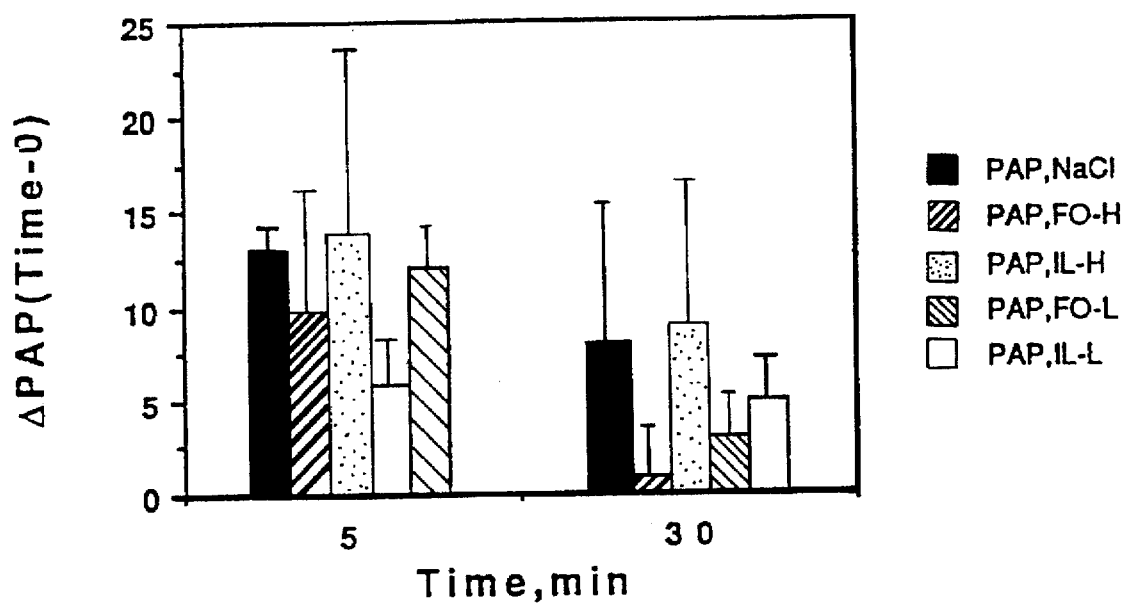

1. Observations during the kallikrein infusion:

All animals had a fast rise in PAP, see FIG. 5, during the kallikrein infusion. The increase in PAP was less pronounced among the MO-em pretreated animals. All animals did also show a decrease in BP. The most pronounced decrease in BP was seen in the high MO-em pretreated animals. No major changes were observed in HR, WP, CO or $PaO_2$ during this period.

2. Observations during the 180 minute post-Kallikrein injection period:

BP was restored to approximately the preinfusion values after about 30 minutes. PAP did also show a decline and the value was almost back to preinfusion level after about 180 minutes. Only minor changes were seen in wedge pressure, cardiac output and $PaO_2$ during this period.

EXAMPLE 3

Need of Antioxidants

Syndromes with DIC may include radical reactions. Oxygen and hydroxy radicals may induce lipid peroxidation of PUFA in cell membranes which as a consequence may lead to cell damage and induction of the cascade systems. Therefore it is important to protect the PUFA in the emulsion, during the administration and after incorporation into biological membranes. The present experiment describes the evaluation of the need of antioxidants to the marine oil emulsions.

Marine oil emulsions (MO-em) (see Example 1) were infused intravenously 20 hours/day to rats over 14 days. The MO-em:s differed in the type of antioxidant added. The daily dose was 25 ml (5 g TG)/kg body weight (b.w.) and the experimental groups were: A) MO-em without antioxidant;, B) MO-em with a-tocopherol (vitamin E), 1 mg/g MO; C) MO-em with a-tocopherol, 1 mg/g MO, and vitamin C, 5 mg/g MO; D) MO-em with a-tocopherol, 5 mg/g MO; E) Intralipid® 20%; F) Physiological saline.

The results were the following;

1) Body weight, weight gain and organ weights (liver, spleen, kidney, lung, myocard, thymus) were similar in all groups.

2) The plasma level of vitamin E was lower in Group A but higher in Group D than in Groups E and F. The level of vitamin C in plasma did not change.

3) The level in the liver of malondialdehyde, MDA, a marker of lipid peroxidation, was higher in Group A compared to all other groups.

4) Histopathological changes consisted mainly of fatty changes in the liver. In Groups A–D these changes were more evident in the Kupffer cells than in the hepatocytes contrary to the findings in Group E. The granulomatous reaction in the liver was more pronounced in Group D than in the other groups.

EXAMPLE 4

Dose-Response Sturdy

Marine oil containing a high degree of ω3-fatty acids has anti-thrombotic and anti-inflammatory effects and effects on hemostasis and immune defence. In order to facilitate a more specific use of the ω3-fatty acids it is important to have information about the dose-response relationships for the various effects and possible side effects. The aim of this study was to evaluate the dose-response relationship for effects of the ω3-fatty acids on fatty acid incorporation, eicosanoid level (inflammation), hemostasis, immune defence and safety. Dose-response relationships for biological effects induced by marine oil (MO)-emulsions, containing different amounts of marine oil triglycerides, (see Example 1) were evaluated. Three different 20% MO-emulsions, of which the composition of the oil was 100% (w/w)MO (Group A); 50% MO+50% soybean oil (SBO) (Group B); 10% MO+90% SBO (Group C) were infused intravenously to rats. The effects were compared with those induced by Intralipid® 20% (Group E) and physiological saline (Group F). The daily dose, 25 ml (5 g TG)/kg body weight (b w) in all groups was infused during 20 hours/day to rats during 14 consecutive days. All MO-emulsions contained α-tocopherol, 1 mg/g oil.

The results were as follows:

1) EPA and DHA in liver and spleen lipids increased dose-dependently in Groups A-C, whereas arachidonic and linoleic acids decreased, compared to Group F. Intralipid® (Group E) induced the opposite changes in these fatty acids. The fatty acid pattern was "normalized" by a low dose of MO-emulsion (Group C).

2) Red blood cell viscosity was reduced to a similar degree by the different MO-emulsions in Groups A–C.

3) The level of thromboxanes, which are prothrombotic in blood, was dose-dependently reduced by the different MO-emulsions with the threshold level in Group C.

4) MO-emulsion in the highest dose was more immuno-suppressive than Intralipid®. Proliferation of splenic cells and thymocytes (3H-thymidin incorporation after Con A stimulation) was depressed more in group A, but similarly in Groups B and C, compared to Group E.

5) Final body weight, weight gain and the relative weights (g/kg b.w.) of liver, spleen and kidney were slightly higher in Groups A and B than in Groups E and F.

6) The degree and nature of fatty changes in Group C were similar to, whereas those in Groups A and B were somewhat more pronounced than those in Group E. The histopathological changes were considered to be slight and probably of no clinical relevance.

7) The mount of lipids in liver and spleen was similar in all groups.

8) The level of malondialdehyde, MDA, a marker of lipid peroxidation, was lower in Groups C and E and similar in Groups A and B to those in Group F.

9) The level in blood of vitamin E (α-tocopherol) was similar in Groups A–C to that in Groups E and F.

The results show that a relatively low dose of MO-emulsion can be chosen to increase the membranal content of ω3-fatty acids and reduce the RBC viscosity, leading to improved nutritive circulation, without risking the less desirable ones (immuno-suppression, histopathological changes, lipid peroxidation). A somewhat higher dose is needed for reduction of the level of thromboxanes.

SUMMARY

DIC is still frequently seen in combination with major trauma, septicemia, meningoencephalitis and pancreatitis. There is often however a 12–26 hours elapse between the onset of symptoms and the debut of coagulation and respiratory distress. Major efforts are today spent on therapeutic manoeuvres in order to prevent these disorders from appearing; early fracture stabilisation, antibiotics, pain management, stress reduction and the goal is also to optimize oxygen delivery. Prophylactic heparin therapy is also sometimes given. Still these syndromes appears in a non-systematic fashion and with a high frequency of most complicated course. Therefore it is most interesting, if some therapy could be given in advance to most patients at risk, with the potential effect of lowering the incidence of DIC.

We have now found that preparations containing ω3-fatty acids have advantageous effects in the treatment of DIC, which may be a symptom as such or included in other symptoms such as sepsis or ischemia. The effects of ω3-fatty acids are seen very early, already after two hours of infusion, and can thus be of value to reduce the incidence of, and as a treatment of the DIC syndrome which is mostly an acute situation. The effects of MO-emulsion in comparison to the control and Intralipid® are summarised in the table below.

TABLE 1

Positive effects of Mo-em in comparison to the control and to Intralipid ®

| Parameter | Effect of KK in the control group | At time post-KK (min) FO-H | Effects of Marine oil emulsion | | | | Positive effects of MO |
|---|---|---|---|---|---|---|---|
| | | | in comp. to placebo FO-L | in comp. to placebo FO-H | in comp. to Intralipid ® FO-L | | |
| PAP | ↑ | 5–30 | ↓ | ↓ | ↓ | ↓ | Reduced vascular resistance |
| TPA | ↑ | 0–90 | ↑ | ↑ | ↑ | ↑ | Increased fibrinolysis |
| APL | ↓ | 180 | ↓ | ≈ | ↓ | ↓ | Increased fibrinolysis |
| FBG | ↓ | 0–180 | ↓ | ≈ | ↓ | ↓ | Reduced vulnerab. to |
| PL.AG. | — | 0[1] | ↓ | ↓ | ↓ | ↓ | Antithrombotic effect |
| FIBRIN DE-POSITS | ↑ | 180 | ↓ | ↓ | ↓ | ↓ | Reduced DIC symptomes |

[1]post. emulsion inf. (0'): ↓ lower; ↑ higher; ≈ similar; — no effect

An improvement of the DIC-syndrome was seen already after a two hours infusion of marine oil emulsion. The positive effects on hemostasis and DIC are obtained after a short single infusion, which together with the anti-inflammatory effects expected after repeated infusion may have wide implications on DIC related syndromes.

After two hours of infusion of marine oil emulsion the increase in PAP, induced by kallikrein-DIC, was reduced, indicating reduced ventilatory complications associated with DIC in the lungs. The reduction of the kallikrein induced increase in PAP and the reduction of MAP seen after infusion of MO-em indicates vasodilation induced by ω3-fatty acids. This effect may be explained either by reduced local production of TXA2 or induction of the release of NO. The results indicate that a short term infusion of a high dose of MO-em concomitant to an increase in plasma kallikrein and induction of DIC induces release of NO. The fibrinolytic response was increased and no fibrin deposits could be found in any of the organs tested (kidney, lung, heart and spleen). These end-point effects (reduced PAP, increased fibrinolysis, no fibrin deposits) show that the magnitude of the induced DIC symptoms was reduced. The tendency of the platelets to aggregate was minimized, indicating reduced risk of thrombosis. This effect may be explained by reduced TXA2 production in platelets or stimulated release of NO in endothelial cells. The reduced level of fibrinogen, seen after only two hours of infusion of marine oil emulsion, may together with other positive effects shown for ω3-fatty acids minimize the vulnerability for heart attacks. $PaO_2$ was maintained. The reduction in RBC viscosity suggests increased nutritional blood flow through capillaries. The positive effects on hemostasis are obtained before, and with a lower dose than that needed to suppress the immune defence. Thus, by a short-term high dose of marine oil emulsion or long-term dosing of a mixture of marine oil and a vegetable oil in emulsion, the risk for immunosuppression is minimized. The effects seen after infusion of MO-em were dose-related and positive in comparison to the changes induced by kallikrein injection in the control and Intralipid® groups.

We have also shown that the addition of dl-α-tocopherol, 1 mg/g oil, is enough to counteract the peroxidation of the highly polyunsaturated fatty acids from marine oil and the reduction of endogenous α-tocopherol and vitamin C induced by MO-em. Furthermore, we have shown that the positive effects of ω3-fatty acids on DIC were obtained when administered together with an antioxidant, α-tocopherol. From these results it may be concluded that the MO-em studied, containing dl-α-tocopherol, 1 mg/g oil, does not induce lipid peroxidation and is efficacious on DIC.

The positive effects of ω3-fatty acids on DIC are obtained after a single dose and before a reduction on the eicosanoid level is obvious. Thus, a low dose can be expected to be effective during long term treatment. If the dose is increased a reduction in eicosanoid synthesis and thereby the anti-inflammatory effect is obtained. This anti-inflammatory effect is in favour over that obtained with NSAID:s, since these drugs block only cyclooxygenase and thereby provide more substrate for the lipoxygenase pathway, leading to enhanced monocyte activation as expressed by increased lipoxygenase effects and induced tissue factor activity. A concomitant vasodilation and increase in nutritional blood flow, reduction in PAP, and maintained $PaO_2$, is a great and unexpected advantage compared to present treatment with vasodilators, which usually reduce $PaO_2$. Marine oil emulsions or other preparations containing ω3-fatty acids can thus be therapeutically useful to treat severe tram and to help to prevent the development into various forms of DIC. Such emulsions can also be useful nutritionally for example to patients with DIC, or to patients vulnerable to the development of DIC, who also need TPN or in long term TPN, to reduce the symptoms of or to help to prevent the development into more chronic forms of DIC.

| ABBREVIATION LIST | |
|---|---|
| AA | Arachidonic acid |
| B.w. | Body weight |
| BP | Blood pressure |
| CO | Cardiac output |
| ConA | Concanavalin A |
| DHA | Docosahexaenoic acid |
| DIC | Disseminated intravascular coagulation |
| EDRF | Entothelial derived relaxing factor |
| EPA | Eicosapentaenoic aicd |
| FM | Fibrin monomer |
| HE | Haematoxylin-eosin |
| IL-I | Interleukin I |
| IL | Intralipid ® |
| IL-H | Intralipid, high dose |
| IL-L | Intralipid, low dose |
| KK | Kallikrein |
| LPS | Lipopolysacharides |
| LVP | Left ventricular pressure |
| MAP | Mean arterial pressure |
| MDA | Malondialdehyde |
| MO | Marine oil |
| MO-em | Marine oil emulsion |
| MO-H | Marine oil emulsion, high dose |
| MO-L | Marine oil emulsion, low dose |
| MOF | Multiorgan failure |
| MSB | Martius scarlet blue |
| MUM-PGI | Main urinary metabolit of prostacyclin |
| MUM-TXA | Main urinary metabolit of thromboxane |
| NO | Nitric oxide |
| NSAID | Nonsteroidal anti-inflammatory drugs |
| PaO2 | Arterial pressure of oxygen |
| PAP | Pulmonary artery pressure |
| PCWP | Pulmonary capillary wedge pressure |
| PTAH | Phosphotungstic acid haematoxylin |
| PUFA | Polyunsaturated fatty acids |
| RBC | Red blood cells |
| t-PA | Tissue plasminogen activator |
| TF | Tissue factor |
| TG | Triglycerides |
| TNF | Tumor necrotic factor |

| ABBREVIATION LIST | |
|---|---|
| TPN | Total parenteral nutrition |
| WP | Wedge pressure |

We claim:

1. Method of treating or preventing a pathological increase in pulmonary arterial pressure (PAP) in a patient in need thereof said PAP being induced by vasoactive mediators not involving thromboxane A2, which comprises administering to said patient in need thereof a preparation containing an effective amount of ω3-fatty acid, a salt or a derivative thereof in order to affect vasoactive mediators other than those involving thromboxane A2.

2. Method according to claim 1 wherein said ω3-fatty acid, salt or derivative thereof is derived from marine oil or from vegetable oil or from phospholipids.

3. Method according to claim 1 wherein said preparation is in the form of an aerosol for inhalation, a dosage form for nasal application or in a dosage form for oral or peroral administration.

4. Method according to claim 1 wherein said preparation also contains an antioxidant.

5. Method according to claim 1 wherein said ω3-fatty acid is selected from the group consisting EPA, DHA, salt thereof, derivative thereof and mixtures thereof.

6. Method according to claim 1 wherein said preparation is in the form of a tablet or capsule for oral or peroral administration.

7. Method according to claim 1 wherein the preparation containing ω3-fatty acid is adapted for total parenteral nutrition and optionally comprises ω6-fatty acid.

8. Method according to claim 1 wherein said preparation is adapted for long-term treatment.

9. The method of claim 1 wherein said preparation is an emulsion comprising 0.5–50% (w/v) of an oil; 0.1–80% (w/v) of a phospholipid, at least 0.5% (w/v) of said ω3-fatty acid or salt or derivative thereof.

10. The method of claim 9 wherein said oil is present in an amount of 5–30% (w/v) and said phospholipid is present in an amount of 0.1–20% (w/v).

11. The method of claim 4 wherein said antioxidant is selected from the group consisting of α-tocopherol, vitamin C, a carotenoid and a retinoid.

12. The method of claim 1 wherein said preparation is administered intravenously.

* * * * *